Figure 1:
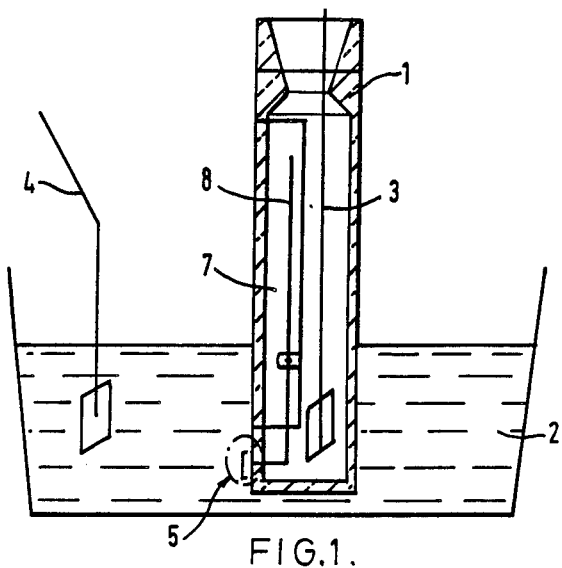

United States Patent [19]

Holley

[11] Patent Number: 4,853,618
[45] Date of Patent: Aug. 1, 1989

[54] PARTICLE COUNTER WITH VARIABLE SIZED APERTURE

[76] Inventor: John E. F. Holley, 9 Shipfield Close, Tatsfield, Nr. Westerham, Kent, Great Britain

[21] Appl. No.: 26,319

[22] Filed: Mar. 16, 1987

[30] Foreign Application Priority Data

Mar. 14, 1986 [GB] United Kingdom ............... 8606299

[51] Int. Cl.⁴ .......................................... G01N 27/00
[52] U.S. Cl. .................................. 324/71.4; 324/425
[58] Field of Search .................. 324/71.4, 71.1, 438, 324/439, 447, 425; 73/861.62, 861.67

[56] References Cited

U.S. PATENT DOCUMENTS 1,326,998  1/1920  Wallace ..................... 73/861.62 X
3,122,431  2/1964  Coulter et al. .................... 324/71.4

Primary Examiner—Reinhard J. Eisenzopf
Assistant Examiner—Robert W. Mueller
Attorney, Agent, or Firm—Fleit, Jacobson, Cohn, Price, Holman & Stern

[57] ABSTRACT

In a particle counter of the Coulter Counter type the orifice size can be varied by the insertion of an insert into the orifice. This enables particles of a wide ranged of sizes to be effectively detected.

5 Claims, 3 Drawing Sheets

PARTICLE COUNTER WITH VARIABLE SIZED APERTURE

The invention herein relates generally to apparatus for analyzing particles in liquid suspensions in accordance with the Coulter Method and more particularly is concerned with the construction of the scanner element or aperture tube for such apparatus.

The Coulter apparatus is well known throughout the world. It comprises apparatus for causing a suspension of microscopic particles to flow through a minute aperture while at the same time an electric current is flowing through the aperture. Each time that a particle passes through the aperture it changes the effective impedance of the body of liquid which is subjected to the influence of the field in the aperture and thereby produces a signal which can be detected for making studies of population, concentration, size etc of the particulate system in suspension.

The apparatus includes a body of sample suspension retained in a vessel of insulating material and a so-called aperture tube immersed in the vessel. The aperture tube has a small wafer set into its wall close to the bottom of the tube, which is usually made of glass or plastic, the wafer commonly being made of corundum or saphire glass, and the interior of the aperture tube is filled with liquid also. The usual arrangement includes a closed, liquid system of which the interior of the aperture tube comprises a part. Such a system provides for means to cause the flow of the suspension from the outer vessel through the aperture in the aperture tube while an electric current also flows through the aperture. There is an electronic detector which is coupled to the respective bodies of liquid on the interior and exterior of the aperture tube by means of metal electrodes immersed in the respective bodies of liquid. The source of electric current is also connected to these electrodes preferably platinum.

The aperture which is formed in the aperture tube is a minute hole in a corundum wafer (commonly used is a watch makers jewel) that is set into the wall of the tube. The aperture tube becomes a scanner element since it scans the liquid flowing through the aperture and produces a measurable signal each time that a particle passes through.

The presence of an electric current passing through the aperture produces a concentrated electric field in a zone which includes the entire aperture and slight bulges at its opposite ends. The current density outside of this zone is so small as to be practically negligible, spreading through the relatively large volume of electrolyte of the two liquid bodies in which the electrodes are immersed. This zone, which may be called a sensing zone, is the volume of electrolyte whose impedance is changed by the presence of particle. If the energy in the sensing zone is provided by a low frequency source of electrical current and the effective electrical impedance of the particles is several orders of magnitude removed from that of the electrolyte (which is practically the case most of the time), then the change in impedance of the effective volume of the sensing zone by the introduction of the particle thereinto will produce a signal which can be detected which is substantially independent of the shape and orientation of the particle. The principle described above signifies that the signal is proportional to the size or volume of the particle. The linearity of response versus particle size is best under conditions that the particles are small with respect to the aperture, for example, having effective diameters less than ten percent of the aperture diameter. Above that size, departure from linearity becomes more apparent but not to the extent that corrections cannot be made in results.

The types of particles which have been analyzed by means of this type of apparatus cover a very wide gamut and include biological and industrial particles, as well known in this art. In any given study, one will choose an aperture diameter to provide fairly linear output for the largest particles which are expected to be involved, but this choice is a compromise with the desire to detect the smallest useful particles as well. In the latter case, the aperture cannot be too large because its sensitivity decreases with increase in size. This should be obvious, since the current density decreases for larger apertures. The length of the aperture is generally made about 70 to 100 percent of its diameter, primarily to give the central region of the electric field within the aperture an opportunity to become fairly uniform. It has been mentioned above that the field bulges at the ends of the aperture giving effects which decrease the sharpness of the signal and its uniformity. The average length of an aperture in the past is about 75 percent of its diameter.

Longer apertures provide problems which offset their advantages. The advantages are a small increase in field uniformity in the center of the aperture and a decrease in the required band width of the amplifiers used in the detector used with the apparatus. The disadvantages are the greater likelihood that coincidence of more than one particle in the aperture will occur, an increased likelihood of debris plugging the aperture with greater difficulty of dislodging the debris, and an increase in the resistance of the longer path. These latter disadvantage are of especially greater importance since it relates to the invention herein.

Increased resistance in the aperture will generate more so-called Johnson noise than a lower resistance of a shorter path thus cancelling the gain to be achieved due to decreased band width of the amplifier. The increased resistance also is part of the problem of heating of the electrolyte as it passes through the aperture. The current density in the aperture is very high and the electrolyte remains under this influence for a longer time than in the case of shorter apertures. Heating of the electrolyte will cause it to produce noise components of a random nature above the normal Johnson noise, limiting the size of particles which can be detected to those which are large enough to produce signals greater than the noise. Additionally, should the temperature of the electrolyte rise above the boiling point, small bubbles will be generated in the aperture and these appear as particles to the detector.

It should be recognized that while the Johnson noise of the contents of the aperture is relatively constant for the rather narrow range of temperatures normally encountered, being proportional to the square root of the temperature on the Kelvin Scale the electrical signal generated by the passage of a particle is proportional to the intensity of the aperture current. If these were the only considerations, it would be possible to detect any particle so long as it exceeded by several orders of magnitude the ionic dimensions of the electrolyte used and displaced enough ions to cause a discernible change over and above the random fluctuation in the number of ions in the sensing zone. The heating of the electrolyte, however, eventually limits the usefulness of increased aperture current as will be seen hereinafter.

The corundum watch maker jewels which are manufactured with sharp-edged inlets are classically used for particle counting. The effect of such sharp-edged inlets upon the flow of liquid through the aperture is to produce a pattern of flow that is known as vena contracta. The flow pattern commences to constrict at the entrance and grows progressively smaller downstream of the entrance, leaving a space between the vena contracta and the wall of the aperture in which the electrolyte has no definite velocity, certainly not the average velocity of the stream passing through the axis of the aperture. The total flow is in fact of the laminar flow type. The electrolyte in this region has eddy currents in that part being swept out (by reason of proximity to the vena contracta) being replaced by electrolyte which enters the region from the downstream end of the aperture next to its wall. This effectively stagnant region has no organized flow pattern and has substantially less motion than the main flow of liquid.

Simultaneously with fluid flow, there is an electric current flowing in the aperture, generating heat in the electrolyte. The temerature of any volume increment of electrolyte rises in accordance with its stay in the region of high current density. It follows that the central laminar flow of the vena contracta will produce the coolest electrolyte but that the electrolyte in the quasi-stagnant region will have increments of electrolyte of higher temperatures and of differing temperatures depending upon how long they remain in the aperture.

The electrical conductivity of an electrolyte varies with its temperature quite rapidly. For instance, 0.1 normal solution of potassium chloride at 31° C. has double the conductivity that it has at 0° C. Thus, an appreciable proportion of the contents of the aperture has an unpredictable conductivity when high aperture currents are used, a fact which causes random modulation of the aperture resistance which is in turn interpreted by the apparatus as noise. In addition to the simple modulation of the aperture resistance due to changes in conductivity, the temperature rises in various locations within the aperture may permit the release of occluded gases in the form of microscopic bubbles, which displace electrolyte and hence are interpreted by the apparatus as particles. Volatile electrolyte may boil, as mentioned above and these bubbles produce signals which look like particles. Accordingly, there is an optimum value of aperture current beyond which the phenomena described are intolerable.

From the above discussion, it will follow that the signal-to-noise ratio of the apparatus improves linearly with aperture current for small aperture currents since the noise is constant whereas the signal developed is proportional to aperture current. Sensitivity also increases. The point is reached, however, at which in addition to the Johnson noise, noise due to the heating effects described above, increases at the same rate as the signal, beyond which point no further improvement is gained in the signal-to-noise ratio, noise increases more rapidly than the signal, after this point is reached the signal-to-noise ratio will in fact worsen.

The invention can provide a device which reduces these problems.

According to the invention there is provided a scanner element which comprises a glass or other inert material element of the type capable of being used in a Coulter type counter which element has an orifice through which liquid can pass when the element is placed in a liquid, there being a movable insert capable of being inserted into the orifice so as to reduce the cross-section area through which the liquid can pass.

There are means to cause a potential difference across the orifice which when a conductive liquid is between the electrodes caused a current to flow.

The outer limit of size of the orifice is determined by the need to measure the largest size of particle in the test system. To determine the insert size the smallest particle to be measured sets the parameters, as the insert will leave a cross-sectional area sufficiently small to enable the smallest particle to be measured adequately.

The insert is preferably made of glass although a metal or other conductor or a material coated with a metal or non-conductive substance can be used, the insert can then form an internal electrode, if required.

Methods of inserting the insert into the orifice can be any conventional method for example a lever arrangement operated by e.g. a piezo electric effect or a d.c. servo motor system.

In an automatic system the movement of the insert can be controlled by a micro-processor which responds to the current flowing. By pre-calibration of the micro-processor the insert control can accurately position the insert in the right position.

The impedance across the orifice at any given orifice volume decreases with decreasing particle size. By reducing the volume of liquid in the orifice, the impedance is caused to increase, hence it is possible using the equipment and method of the invention to maintain the impedance within a preferred range for any particle size within a large range of particle sizes. For any given voltage applied across the orifice the impendance controls the current in accordance with ohm's law.

The micro-processor control operates by responding to the current flowing across the orifice (which current is proportional to the volume of liquid in the orifice) in such a way that by pre-setting the micro-processor with approrpriate current values it can be ensured, by a feedback loop, that the insert is inserted into the orifice to the appropriate depth to give the impedance necessary to maintain the desired current flowing and hence a preferred signal to noise (S/N) ratio.

When red and white cells in urine are to be looked at this is done with a 100–70 $\mu$m range of orifices so it is possible to control the blocking and look at red and white cells with a narrow band amplifier for the signal generated. The narrow band amplifier is designed to give the best performance for small particles of 0.7 $\mu$m to 2.1 $\mu$m. However, if a smaller orifice is used e.g. in the 30–50 $\mu$m range and a wide band amplifier is used it would be possible to detect particles of 0.7 $\mu$m to 2.1 $\mu$m but blocking becomes a problem.

The selection of good pulses can be carried out in an analogue CCT or a digital CCT. The selection of good pulses relies on there being sufficient of these particles (pulses) to induce a level for selection of particles of the same size.

Red cell sizes are from about 4 $\mu$m to 12 $\mu$m and white blood cells are from about 12 $\mu$m–24 $\mu$m. By choosing an orifice of sufficient size to accommodate the largest particle size to be measured it is possible to vary the area of the orifice to accommodate the detection of smaller size particles.

Difficulty occurs when there is a range of particles (pulses) of differing sizes. For example urines which are contaminated or are badly taken or are taken when the bladder is releasing cells or parts of cells will give a broad range or band of particle sizes, it is in this band that there are the organisms that are normally sought which cause most difficulties. The ranges from 3,000 up to 500,000 particles are troublesome.

The shape of the piston (insert) could be a rod or similar diameter uniform along its length or it could go from a point and increase in diameter along its length, the cross sectional will be a circle for convenience so as to fit into the round hole of the orifice. At its base it could be slightly smaller than the orifice to be used to help in alignment.

If the diameter of the piston (insert) varies along its length it can do so continuously or it can do so in steps. The steps corresponding to particular diameters of the rod to cause the orifice to have specific diameters which are known to correspond to types of particles.

In order to obtain accurately shaped piston (insert) conventional methods can be used; preferred is using etching by conventional etching processes.

The arm to which the piston can be connected can be a parallel bimorph piezoelectric lever which is arranged so that one end is fixed.

The end connected to the arm and piston is free, but when a dc voltage is passed through the bimorph it will bend thus pushing the piston into the orifice. Alternatively, the piston can be moved by a dc servo motor and cam acting on a lever pivotted at one end, connected to the piston via an arm.

The movement will be arranged so as to place the centre core/piston in such a position which will cause the orifice volume to give the required signal to noise which will be best for the size of particle which is under investigation at that time e.g. no insertion into the orifice when looking for white cells and maximum insertion when looking for low numbers of small cells (organisms).

A second feature is that the dilution will decrease as the orifice gets smaller due to the decrease in the flow of the sample through that smaller orifice. The separation of the particles will therefore be greater and, due to this, it will be easier to detect them against a messy background.

Preferably the piston is inserted into the back of the orifice against the flow of the sample it will not cause the type of blocking of small orifice which has been experienced and the removal of the insert will immediately release any blocking which may occur. The dimension when the piston is removed from the back of the orifice is preferably greater than the largest particle to be dealt with e.g. white cell—10–15 $\mu$m (0.010–0.015 mm) so that when the insert is in its rest position outside the orifice it will be approximately 15–40 $\mu$m away from the back edge of the orifice but still in the stream of the incoming sample (e.g. isotonic salt solution) the pressure can then be arranged so that the laminar flow of the sample will act to keep the piston free of debris.

The design of the total probe is arranged so that a primary setting up of the position of the piston is possible. The arm attached to the insert can be located in a rubber type seal e.g. O rings and its outside part is connected to a pivot type adjustment. The rubber seal or O rings will enable the piston to be positioned in the appropriate place before connection to a DC motor and cam so that the computer control to take over.

A standard electrode inside the probe is preferably used. Alternatively, the piston can be an electrode.

Figure 2:
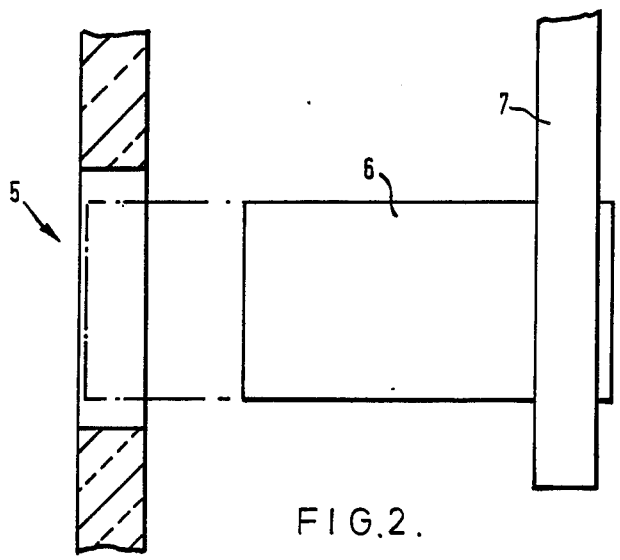
Figure 3:
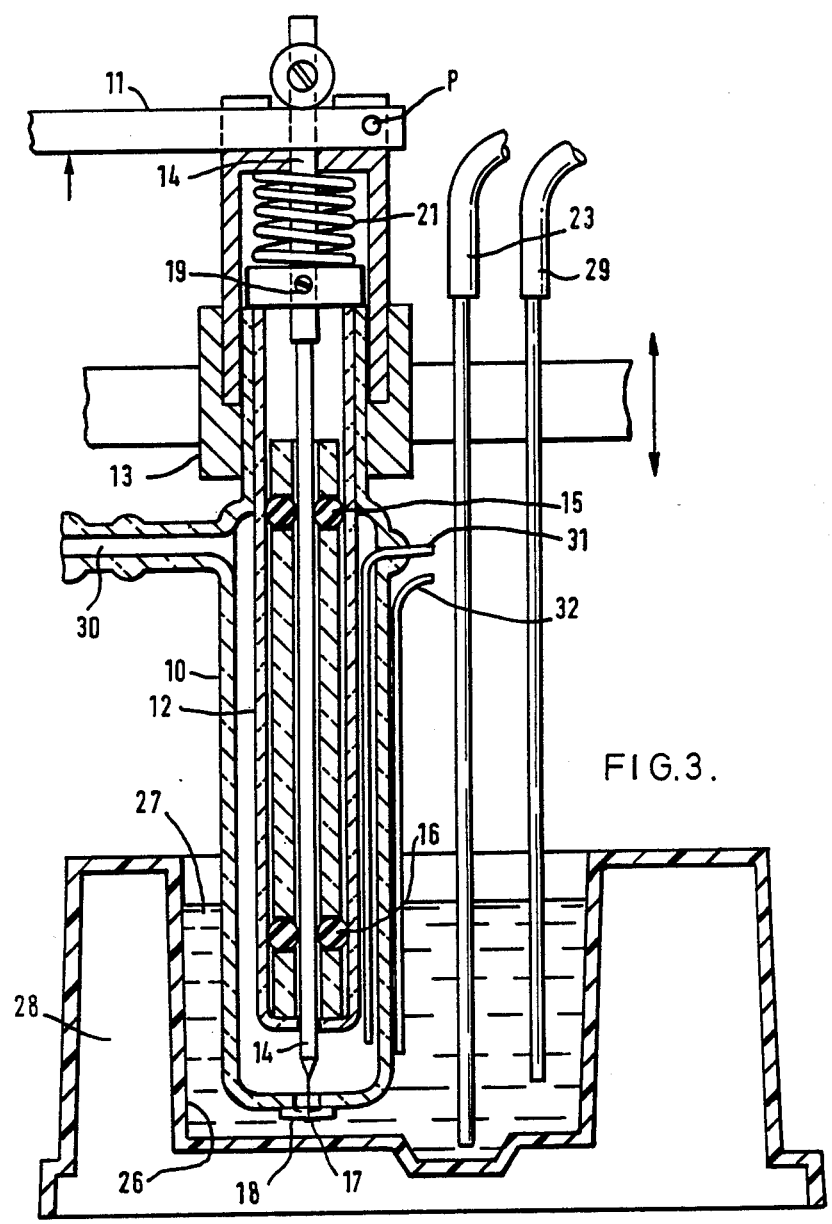
Figure 4:
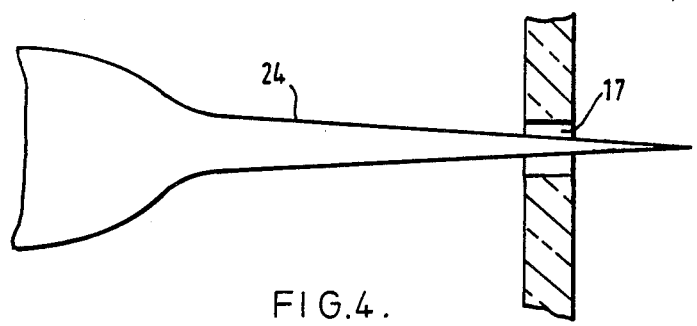
Figure 5:
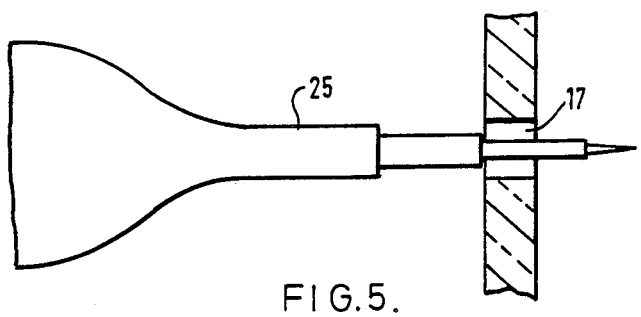

The invention is described with reference to the accompanying drawings in which:

FIG. 1 is a side view of an embodiment of the invention.
FIG. 2 is an enlarged view of the orifice.
FIG. 3 is a different embodiment of the invention.
FIG. 4 is a side view of the insert and orifice.
FIG. 5 is a side view of a different type of insert.

A sampler 1 is placed in salt solution 2 with the test sample. The sampler has an electrode 3 and an external electrode 4. There is an orifice 5 into which a piston 6 (FIG. 2) can fit. The piston 6 is attached to an arm 7 controlled as shown generally at 8.

In operation the piston 6 can be controlled to enter the orifice 5 so as to vary the diameter.

Referring to FIG. 3 a probe body 10 having an orifice in its bottom over which is fixed a glass plate 18. Inside the probe body 10 is an inner tube 12 fixed in position by collar 13 so as to be held rigid and central. Mounted inside the inner tube 12 is a rod or piston 14 which protrudes above the end of the tube 12. The rod is held in position by two neoprene rubber O rings 15 and 16 which can act also as a vacuum seal. The rod 14 can move up and down a small way against the O rings due to the resilience of the O rings, without the vacuum being broken.

Two electrodes 31 and 32 are positioned as shown and are connected via a microprocessor (not shown) to a voltage source. The microprocessor controls the current flow to the driving means moving the arm 11 which moves the rod 14 so as to position the insert 17 in the orifice 18.

The rod 14 can have a stepped end shown in detail in FIG. 2 and is positioned so it fits exactly within the orifice 17 in the plate 18.

At the top end of the inner tube 12 is attached a metal part 19, which contacts a cup 20 and spring 21. The whole assembly is fixed so that the rod cannot move down too far to damage the orifice and the rod stays positioned very accurately in relation to the orifice.

A pivotted arm 11 is fixed to the top of the rod 14. The pivot is shown at 21. By movement of the pivot arm 11 against the spring 21 the end of the rod 14 is moved in and out of the orifice 17.

Referring to FIGS. 4 and 5. In FIG. 4 is shown a rod end 24 which varies continuously and FIG. 5 is shown a stepped rod end 25. Referring to FIGS. 4 and 5 it can be seen that movement of the rod alters the surface area between the rod and orifice and effectively varies the orifice diameter.

Referring to the rest of FIG. 3, the probe is shown in a plate 28 in which there is a well 26. In the well there is a liquid 27. The well can be filled by filling tube 28 and emptied by tube 29. There is a tube 30 leading to a suction pump to suck the liquid into the probe body through the orifice.

EXAMPLE

The equipment shown in FIG. 3 was set up. The circular orifice had a diameter of 70 $\mu$m, the insert was of the shape shown in FIG. 4 and its diameter varied from 30 $\mu$m to 60 $\mu$m.

Isotonic liquids containing 5 $\mu$m and 0.5 $\mu$m beads were placed in the well and without the insert in place, the liquid was sucked through the orifice. This was repeated with the microprocessor operating to control the insert position to optimise the S/N ratio.

The two electrodes are connected via an ARC 2682 turbo microprocessor at a voltage of 40 volts. The output from the microprocessor was fed to an oscilloscope which could measure the voltage by means of a height of pulse between the electrodes caused by the non-conductivity of the latex beads.

The following results were obtained.

| Bead Size | No. insert Pulse height | Insert Position adjusted by Microprocessor |
| --- | --- | --- |
| 5 μm | 0.5 volts | 1.0 volts |
| 0.5 μm | no reading | 0.1 volts |

The oscilloscope scale can be adjusted to give a measurable pulse height appropriate for the voltage.

This Example shows that the method and apparatus of the invention can cause a larger reading to be obtained with the larger particles and with particles too small to be detected by conventional equipment (i.e. with no insert) the same equipment can detect otherwise undetectable particles.

I claim:

1. A particle counter which incorporates an element which comprises a body having an orifice through which liquid can pass, wherein, mounted within the body, is a moveable support means having an insert attached thereto, the insert being positioned so as to be able to move in and out of the orifice and further in which there are means to develop a potential difference across the orifice and means for measuring the change in the potential difference.

2. A particle counter as claimed in claim 1 in which the said means to develop the potential difference across the orifice comprise two electrodes mounted either side of the orifice and there are means to measure the change in the potential difference between the electrodes.

3. A particle counter as claimed in claim 1 in which the said support means is driven by an electrical driving means controlled by a microprocessor which processor is connected to the said means for passing an electric current across the orifice so as to automatically move the probe in relation to the orifice in accordance with the current flowing across the orifice.

4. A particle counter which comprises a body having an orifice through which liquid can pass, two electrodes positioned either side of the said orifice, means for developing a potential difference between the electrodes, a support means having an insert of substantially circular cross section attached thereto, which support means is moveably mounted within the said body and positioned so the insert can be inserted into the orifice, the said support means being electrically driven by a driving means controlled by a microprocessor, which microprocessor is operated in response to the potential difference between the said electrodes, and a signal detection means which measures the change in the potential difference between the said electrodes, the said insert varying in diameter along its length.

5. A method of analysing particles in liquid suspension in which the liquid is passed through an orifice across which an electric current flows and the impedance across the orifice is measured, characterised in that an insert is inserted in the orifice if the impedance measured is outside a predetermined range and in that the depth of insertion is controlled to give a predetermined impedance measurement.

* * * * *